United States Patent [19]

Higgens et al.

[11] 4,024,246

[45] May 17, 1977

[54] ANTIBIOTIC A-22082 AND PROCESS FOR PRODUCTION THEREOF

[75] Inventors: Calvin E. Higgens; Karl H. Michel, both of Indianapolis, Ind.

[73] Assignee: Eli Lilly and Company, Indianapolis, Ind.

[22] Filed: Aug. 25, 1976

[21] Appl. No.: 717,739

Related U.S. Application Data

[63] Continuation-in-part of Ser. No. 619,108, Oct. 2, 1975, abandoned.

[52] U.S. Cl. .............................. 424/119; 195/80 R
[51] Int. Cl.² ........................................ A61K 35/74
[58] Field of Search ................... 424/119; 195/80 R

[56] References Cited

OTHER PUBLICATIONS

Benz et al., *Helv. Chim. Acta,* vol. 57 (8) pp. 2459–2477 (1974).
Derwent, No. 75844w, *Abstracting,* CH568386, published 10/31/75.

*Primary Examiner*—Jerome D. Goldberg
*Attorney, Agent, or Firm*—Nancy J. Harrison; Arthur R. Whale

[57] ABSTRACT

Antibiotic A-22082 is produced by submerged aerobic fermentation of *Aspergillus nidulans* NRRL 8112. Antibiotic A-22082 is an antifungal agent.

3 Claims, 1 Drawing Figure

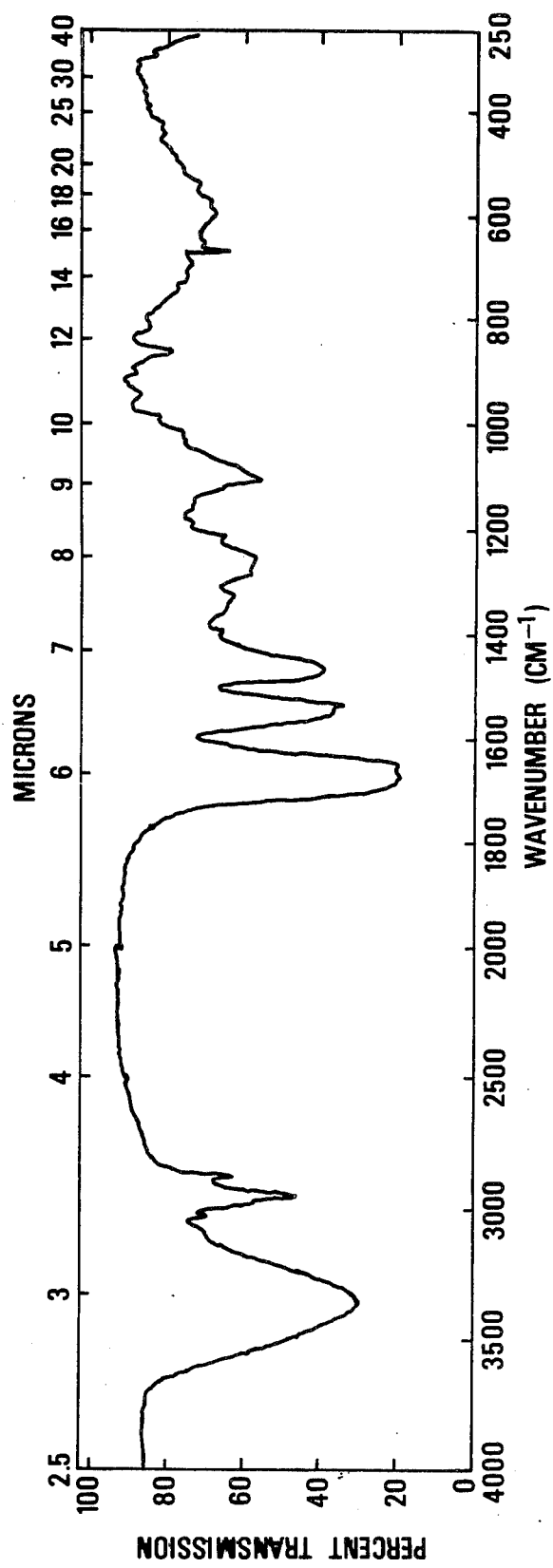

ANTIBIOTIC A-22082 AND PROCESS FOR PRODUCTION THEREOF

CROSS-REFERENCE TO RELATED APPLICATION

This is a continuation-in-part of copending application Ser. No. 619,108, filed Oct. 2, 1975 now abandoned.

SUMMARY OF THE INVENTION

This invention relates to a new polypeptide antibiotic which is produced by culturing a hitherto undescribed strain of the organism *Aspergillus nidulans* NRRL 8112. The new antibiotic of this invention is arbitrarily designated herein as antibiotic A-22082.

Antibiotic A-22082 is produced together with several minor factors as a complex which is arbitrarily designated as the A-22082 antibiotic complex. The A-22082 antibiotic complex is produced by culturing a novel strain of *Aspergillus nidulans* NRRL 8112 under submerged aerobic fermentation conditions until a substantial level of antibiotic activity is produced. The A-22082 antibiotic complex is separated from the fermentation medium by extraction with polar organic solvents. The A-22082 antibiotic complex is further purified, and antibiotic A-22082 is isolated by the use of a variety of techniques such as chromatography.

Antibiotic A-22082 is an antifungal agent.

DESCRIPTION OF THE DRAWING

The infrared absorption spectrum of antibiotic A-22082 in KBr disc is presented in the accompanying drawing.

DETAILED DESCRIPTION OF THE INVENTION

ANTIBIOTIC A-22082

Antibiotic A-22082 is a white amorphous solid. Elemental analysis of A-22082 gave the following approximate percentage composition:

carbon, 56.52%; hydrogen, 7.29%; nitrogen, 8.68%, oxygen, 27.09%. The approximate empirical formula proposed for antibiotic A-22082 is $C_{51-53}H_{79-83}N_7O_{17-19}$. Within this approximate range, the elemental analysis of antibiotic A-22082 corresponds especially well with an empirical formula of $C_{52}H_{81}N_7O_{18}\cdot H_2O$. (Calcd.: C, 56.24; H, 7.54; N, 8.84; O, 27.39).

Antibiotic A-22082 has an approximate molecular weight of 1100, as determined by mass spectrometry and titration.

The infrared absorption spectrum of antibiotic A-22082 in KBr disc is presented in the accompanying drawing. The following characteristic absorption maxima are observed: 2.97 (strong), 3.30 (weak), 3.36 (shoulder), 3.39 (medium), 3.47 (weak), 5.97 (strong), 6.06 (strong), 6.45 (medium), 6.53 (medium), 6.83 (medium), 7.78 (weak), 8.00 (weak), 9.07 (weak) and 11.66 (weak) microns.

The ultraviolet absorption spectra of antibiotic A-22082 in both neutral and acidic methanol exhibit absorption maxima at 225 nm ($\epsilon$ 18,000), 275 nm ($\epsilon$ 3,000) and 284 nm (shoulder $\epsilon$ 2,500). The ultraviolet spectrum of antibiotic A-22082 in basic methanol shows absorption maxima at 245 nm ($\epsilon$ 16,000) and 290 nm ($\epsilon$ 3,000) and also end absorption.

The $^{13}C$ nuclear magnetic resonance spectrum of antibiotic A-22082 in perdeuteromethanol showed the following characteristics:

$\delta$ 176.1, 174.3, 173.4, 172.7, 172.4, 169.8, 158.4, 132.8, 130.9, 129.6, 129.0, 116.2, 77.0, 75.7, 74.4, 71.3, 70.9, 69.6, 68.3, 62.4, 58.7, 56.9, 56.1, 52.9, 39.0, 38.5, 36.8, 35.2, 33.9, 32.9, 32.6, 30.7, 30.4, 30.2, 28.2, 27.0, 26.5, 23.6, 20.1, 19.6, 14.4, and 11.3 ppm.

Antibiotic A-22082 has the following specific rotations:

$[\alpha]_D^{25}$ $-44°$ (c0.5, $CH_3OH$)
$[\alpha]_{365}^{25}$ $-156°$ (c0.5, $CH_3OH$)

Electrometic titration of antibiotic A-22082 in 66% aqueous dimethylformamide indicated the presence of a titratable group with a $pK_a$ value of 12.7 (initial pH 6.9).

Amino-acid analysis of antibiotic A-22082 indicated the presence, after hydrolysis, of threonine, hydroxyproline and three other as-yet-unidentified amino acids.

Antibiotic A-22082 is soluble in a variety of organic solvents such as methanol, ethanol, dimethylformamide, dimethyl sulfoxide, and ethyl acetate; but is insoluble in nonpolar organic solvents such as diethyl ether and petroleum ether. Antibiotic A-22082 is also soluble in aqueous solutions, especially those having a pH greater than 7.0.

Antibiotic A-22082 has an $R_f$ value of 0.35 on silica-gel thin-layer chromatography using a benzene:methanol (7:3, v:v) solvent system and *Candida albicans* bioautography for detection. Antibiotic A-22082 also has the following $R_f$ values in the paper chromatographic systems indicated below, using *Candida albicans* bioautography for detection:

| $R_f$ Value | Solvent System |
|---|---|
| 0.76 | Butanol saturated with water |
| 0.69 | Butanol saturated with water plus 2% p-toluenesulfonic acid |
| 0.75 | Methanol:0.1 N HCl (3:1) |
| 0.17 | Butanol:ethanol:water (13.5:15:150) |
| 0.78 | Methanol:0.05 M sodium citrate at pH 5.7 (7:3); paper buffered with 0.05 M sodium citrate at pH 5.7 |

Antibiotic A-22082 is very similar to the polypeptide antibiotic Echinocandin B reported by F. Benz et al., *Helv. Chim. Acta* 57, 2459-2477 (1974) except that Echinocandin B is reported to be inactive against dermatophytes. A-22082 is active against dermatophytes.

Antibiotic A-22082 is produced by culturing an A-22082-producing strain of *Aspergillus nidulans* under submerged aerobic conditions in a suitable culture medium until a substantial amount of antibiotic activity is produced.

One organism useful for the preparation of antibiotic A-22082 is classified as a strain of *Aspergillus nidulans* (Eidam) Wint., which is in the *Aspergillus nidulans* form group.

Another organism which is useful for the preparation of antibiotic A-22082 is described in a copending application of Hoehn and Michel titled ANTIBIOTIC A-30912 AND PROCESS FOR PRODUCTION THEREOF, Ser. No. 619,107, filed October 2, 1975. Antibiotic A-22082 is produced as a major component, factor A, of the A-30912 antibiotic complex. The A-30912-producing organism is classified as a strain of *Aspergillus rugulosus* Thom and Raper which is also in the *Aspergillus nidulans* form group. Both the above classifications are based on the descriptions of K. B. Raper and D. I. Fennel in "The Genus Aspergillus, " The Williams and Wilkins Company, Baltimore, Md., 1965.

Color names were assigned according to the ISCC-NBS method (K. L. Kelly and D. B. Judd, "The ISCC-NBS Method of Designating Color and a Dictionary of Color Names," U.S. Dept. of Commerce, Circ. 553, Washington, D. C., 1955). The Maerz and Paul color blocks are described by A. Maerz and M. R. Paul in "Dictionary of Color," McGraw-Hill Book Company, New York, N.Y., 1950.

Cultures were grown at 25° C. unless otherwise specified.

CULTURAL CHARACTERISTICS OF A. NIDULANS NRRL 8112 Czapek's Solution Agar

When grown at 25° C. for 2 weeks, the culture attains a diameter of 4.0 cm. The colony is rugulose and has a strongly crenate margin consisting of deeply submerged, brownish yellow hyphae. A colorless exudate, becoming pinkish with age, sometimes occurs. Loosely woven, nearly globose mycelial tufts occur randomly over the surface and in a submarginal line. As these tufts mature, they become more tightly woven and are interlaced with, and eventually enveloped in, hulle cells. Early growth ranges from white to buff, becoming pale yellow green (ISCC-NBS 12 and Maerz and Paul 10-A-1). In two weeks, growth becomes pale orange yellow (ISCC-NBS 73 and Maerz and Paul 10-B-3). After three weeks, widely scattered conidial heads, sometimes occurring in patches, are from white to light yellow initially, then becoming dark grayish yellow (ISCC-NBS 91 and Maerz and Paul 13-11-1). No soluble pigment is evolved. The slightly buckled colony reverse ranges from white to light brown (ISCC-NBS 57 and Maerz and Paul 5-A-10) and darkens with age to dark purplish shades.

Conidial heads are at first radiate, but become short and columnar with age. Young globose heads may be up to $70\mu$ in diameter, but average $60\mu$. Columnar heads are from $75\mu$ to $125\mu$ long and from $30\mu$ to $65\mu$ wide and average $95\mu \times 47\mu$.

Conidiophores, vesicles, and phialides are smooth-walled and pale brown. Conidiophores range in length from $38\mu$ to $56\mu$ but may attain $85\mu$. They are up to $5\mu$ wide.

Vesicles are subglobose to hemispherical and may be terminally flattened. They are generally from $8\mu$ to $11\mu$ in diameter, but average $9.6\mu$.

Sterigmata are biseriate, and secondary sterigmata are frequently in pairs. Primary sterigmata are nearly cuneiform. They range in length from $3.2\mu$ to $6.3\mu$ and average $4.4\mu$. At their widest point they are $2.8\mu$. Secondary sterigmata are flask-shaped and elongate. They are $3.4\mu$ at their widest point and taper to $1\mu$ wide. They range in length from $4.7\mu$ to $7.9\mu$ and average $6.2\mu$.

Conidia are rugulose, globose, yellow to green en masse, and range from $1.6\mu$ to $4.6\mu$ in diameter, averaging $2.5\mu$.

The ascogenous state is encrusted in hulle cells on the colony surface but may also be found at levels beneath the surface. Hulle cells are hyaline and may become pinkish to brownish as cleistothecia develop. The hulle cells are globose to subglobose or oval to elongate and, in general, are from $14\mu$ to $18\mu$ in diameter. Cleistothecia are globose, thick-walled, and are hyaline when young and dark purple when fully mature. They range from $185\mu$ to $320\mu$ in diameter and average $200\mu$.

Asci are hyaline, globose to oval, and may disintegrate before cleistothecia mature. Globose asci are $12.6\mu$ in diameter. Oval asci average $14.1\mu \times 11.1\mu$ and range from $12.6\mu$ to $17.4\mu$ long and from $9.5\mu$ to $12.6\mu$ wide.

Ascospores are smooth walled, orange, and adorned with two delicately pleated, parallel equatorial crests which are unbroken and $0.8\mu$ wide. If the crest is equatorial, it is through the long axis of a lenticular ascospore which is from $4.3\mu$ to $5.1\mu$ long and from $2.7\mu$ to $3.5\mu$ wide and averages $4.5\mu$ to $3.2\mu$. If the crest is peripheral, the ascospore appears globose, and the body has a diameter equal to the length of the lenticular view.

Malt Extract Agar

When grown at 25° C., the culture grows rapidly, achieving a diameter of 5 cm. in 10 days and up to 7 cm. in 3 to 4 weeks. Colonies are velutinous, yellow green. By the seventh day small white clusters of hulle cells occur randomly over the surface and in a submarginal band. The hulle cell clusters become dull yellow with age. The crenate colony periphery consists of deeply submerged yellowish brown hyphae. In general, the surface is moderate olive green (ISCC-NBS 125 and Maerz and Paul 24-L-1), and the colony reverse is moderate olive (ISCC-NBS 107 and Maerz and Paul 15-L-4).

The conidial and the ascogenous states are similar to those of Czapek's solution agar with several exceptions. Vesicles are smaller, ranging from $6.3\mu$ to $11.0\mu$ in diameter and averaging $8.7\mu$. Globose asci are $11.0\mu$ in diameter, and asci are from $11.1\mu$ to $12.6\mu$ long and from $9.5\mu$ to $10.3\mu$ wide, averaging $11.3\mu \times 10.1\mu$. Ascospores average $4.0\mu \times 3.2\mu$.

Certain characteristics of the antibiotic A-22082-producing strain of *Aspergillus nidulans* NRRL 8112 differ from the characteristics of the organism described by Raper and Fennel, supra. The A-22082-producing strain produces smaller conidiophores, conidia, and hulle cells, but slightly larger conidial heads and secondary sterigmata. The A-22082-producing strain produces an exudate, whereas the organism described by Raper and Fennell does not. All other characteristics conform to those of the published description and confirm the identification of the A-22082-producing organism as a new strain of *Aspergillus nidulans* (Eidam) Wint.

The *Aspergillus nidulans* and *Aspergillus rugulosus* cultures useful for the production of antibiotic A-22082 have been deposited and made a part of the stock culture collection of the Northern Regional Research Laboratory, U.S. Dept. of Agriculture, Agricultural Research Service, Peoria, Ill. 61604. The *Aspergillus nidulans* culture is available to the public under the number NRRL 8112, and the *Aspergillus rugulosus* culture is available under the number NRRL 8113.

When the *A. rugulosus* NRRL 8113 culture is used to produce antibiotic A-22082, a separation from co-produced antibiotic factors is required. The seven factors produced by *A. rugulosus* can be separated and identified by the use of thin-layer chromatography (TLC). Silica gel is a preferred adsorbent; and benzene:methanol (7:3) is a preferred solvent system.

The $R_f$ values of the *A. rugulosus* (A-30912) factors A-G (factor A = antibiotic A-22082) using silica-gel (Merck, Darmstadt) TLC, the benzene:methanol (7:3) solvent system, and *Candida albicans* bioautography are given in Table I.

TABLE I

| A-30912 Factor | $R_f$ Value |
|---|---|
| A | 0.35 |
| B | 0.45 |
| C | 0.54 |
| D | 0.59 |
| E | 0.27 |
| F | 0.18 |
| G | 0.13 |

The *A. rugulosus* NRRL 8113 culture produces more antibiotic A-22082, however, than does the *A. nidulans* NRRL 8112 culture. The *A. rugulosus* NRRL 8113 culture is, therefore, a preferred culture for the production of antibiotic A-22082.

The known compound sterigmatocystin is produced by both *Aspergillus nidulans* NRRL 8112 and *Aspergillus rugulosus* NRRL 8113. During the recovery process, sterigmatocystin is extracted together with the antibiotic complexes by extraction of the fermentation media with polar organic solvents. The antibiotic complexes are separated from sterigmatocystin by precipitation techniques.

The culture medium employed to grow *A. nidulans* NRRL 8112 or *A. rugulosus* NRRL 8113 can be any one of a number of media. For economy in production, optimal yield, and ease of product isolation, however, certain culture media are preferred. Thus, for example, a preferred carbohydrate source in large-scale fermentation for *A. nidulans* NRRL 8112 is sucrose, although glucose, maltose, glycerol, and the like may be employed. A preferred carbohydrate source in large-scale fermentation for *A. rugulosus* NRRL 8113 is glucose, although sucrose, molasses, starch, lactose, maltose, and the like may be employed. For *A. nidulans*, preferred nitrogen sources are enzyme-hydrolyzed casein and corn steep liquor. For *A. rugulosus*, preferred nitrogen sources are enzyme-hydrolyzed casein and soluble meat peptone.

Nutrient inorganic salts can be incorporated in the culture media. These include the customary soluble salts capable of yielding sodium, magnesium, calcium, ammonium, chloride, carbonate, sulfate, nitrate, and like ions.

Essential trace elements necessary for the growth and development of the organism should also be included in the culture medium. Such trace elements commonly occur as impurities in other constituents of the medium in amounts sufficient to meet the growth requirements of organism.

It may be necessary to add small amounts (i.e. 0.2 ml./l.) of an antifoam agent such as polypropylene glycol to large-scale fermentation media if foaming becomes a problem.

For production of a substantial quantity of antibiotic A-22082, submerged aerobic fermentation in tanks is preferred. Small quantities of antibiotic A-22082 may be obtained by shake-flask culture. Because of the time lag in antibiotic production commonly associated with inoculation of large tanks with the spore form of the organism, it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transferred to a larger tank. The medium used for the growth of the vegetative inoculum can be the same as that used for larger fermentations, but other media can also be employed.

The A-22082-producing organisms can be grown at temperatures between about 20° C. and about 40° C. Optimum A-22082 production by *A. nidulans* appears to occur at temperatures of about 25°-30° C. Optimum A-22082 production by *A. rugulosus* appears to occur at a temperature of about 25° C.

As is customary in aerobic submerged culture processes, the culture medium is aerated by sparging with sterile air while being mechanically agitated by conventional turbine impellers in a fully baffled vessel. Efficient antibiotic production is obtained when the dissolved oxygen content of the medium is maintained at, or above, 35 percent of air saturation.

The production of antibiotic A-22082 can be followed during the fermentation by testing samples of alcoholic extracts of the whole broth for antibiotic activity against an organism known to be sensitive to the antibiotic. One assay organism useful in testing for the presence of antibiotic A-22082 is *Candida albicans*. The bioassay is conveniently performed by paper-disc assay on agar plates.

Generally, antibiotic activity is detectable on the third day of the fermentation. Maximum production of antibiotic activity usually occurs between about the fourth and the sixth days with *A. nidulans* and between about the third and the sixth days with *A. rugulosus*.

Antibiotic A-22082 is a useful antifungal agent. The antifungal activity of antibiotic A-22082 was demonstrated by in vitro tests. Antifungal activity was measured by the conventional disc-diffusion method (6-mm pads were dipped in solutions containing antibiotic A-22082; pads were placed on agar plates seeded with test organism). Table II summarizes the minimal inhibitory concentration (MIC) per disc at which antibiotic A-22082 inhibited representative organisms.

TABLE II

| Test Organism | MIC (mcg./disc) |
|---|---|
| *Candida albicans* | 0.625 |
| *Trichophyton mentagrophytes* | 0.078 |
| *Candida tropicalis* | 3.12 |

Antibiotic A-22082 is very active in in vitro disc-diffusion tests against dermatophytes. The results of these tests are summarized in Table III.

TABLE III

| ANTIBIOTIC A-22082 VS. DERMATOPHYTES | | |
|---|---|---|
| Dermatophyte | No. of Isolates | MIC (mcg/disc) |
| *Trichophyton mentagrophytes* | 13 | 1.25–0.039 |
| *Trichophyton gallinae* | 1 | >1.25 |
| *Trichophyton meginini* | 1 | 0.0195 |
| *Trichophyton quinckeanum* | 1 | >1.25 |
| *Trichophyton rubrum* | 1 | <.0098 |
| *Trichophyton schoenleinii* | 1 | 0.0195 |
| *Trichophyton terrestre* | 1 | 0.0195 |
| *Trichophyton tonsurans* | 9 | >1.25–0.156 |
| *Microsporium* | | |

TABLE III-continued
ANTIBIOTIC A-22082 VS. DERMATOPHYTES

| Dermatophyte | No. of Isolates | MIC (mcg/disc) |
| --- | --- | --- |
| gypseum | 5 | 0.156–0.039 |
| Microsporium audouinii | 4 | 1.25–0.156 |
| Microsporium canis | 6 | 1.25–0.0098 |
| Microsporium cookei | 2 | 1.25–0.0195 |
| Nannizzia incurvata | 1 | 0.312 |
| Philaphere jean salemi | 1 | >1.25 |
| Epidermatophyton floccosum | 1 | 1.25 |
| Geotrichum candidum | 4 | >1.25–0.156 |
| Keratinomyces ajellio | 1 | 0.156 |

The antifungal activity of antibiotic A-22082 was further demonstrated by in vivo tests. When two doses of antibiotic A-22082 were administered to Candida albicans-infected mice, protection against C. albicans was provided. A measure of the protection afforded is the $ED_{50}$ value [the effective dose in mg./kg. which protects 50 percent of the mice; see W. Wick et al., J. Bacteriol. 81, 233–235 (19610]. The $ED_{50}$ values for antibiotic A-22082 against Candida albicans in mice were 30 mg./kg. (intraperitoneal administration) and 50 mg./kg. (subcutaneous administration).

There were no signs of acute toxicity when antibiotic A-22082 was administered intraperitoneally (ip) or subcutaneously (sc) to mice at 100 mg./kg. twice per day for three days (a total of 600 mg./kg.). There were also no signs of acute toxicity when antibiotic A-22082 was administered ip to mice at 200 mg./kg. 3 times over 24 hours (a total of 600 mg./kg.).

When used as an antifungal agent, antibiotic A-22082 is administered parenterally and is commonly administered together with a pharmaceutically-acceptable carrier or diluent. The dosage of antibiotic A-22082 will depend upon a variety of factors, such as the nature and severity of the particular infection involved.

In order to illustrate more fully the operation of this invention, the following examples are provided.

EXAMPLE 1

A. Shake-flask Fermentation of A-22082 using *A. nidulans* NRRL 8112

A culture of *Aspergillus nidulans* NRRL 8112 was prepared and maintained on an agar slant having the following composition:

| Ingredient | Amount |
| --- | --- |
| Tomato paste | 2 percent |
| Baby oatmeal | 2 percent |
| Agar | 2 percent |
| Deionized water | 94 percent |

The slant was inoculated with *Aspergillus nidulans* NRRL 8112, and the inoculated slant was incubated at 25° C. for about 7 days. The mature slant culture was covered with beef serum and scraped with a sterile loop to loosen the spores. The resulting suspension was lyophilized into six pellets.

One lyophilized pellet thus prepared was used to inoculate 50 ml. of a vegetative medium having the following composition:

| Ingredient | Amount (percent) |
| --- | --- |
| Glucose | 1.0 |
| Glycerol | 1.0 |
| Cottonseed meal | 2.5 |
| $CaCO_3$ | 0.1 |
| Water | 95.4 |

The inoculated vegetative medium was incubated in a 250-ml. Erlenmeyer flask at 25° C. for 48 hours on a shaker rotating through an arc two inches in diameter at 250 RPM.

B. Tank Fermentation of A-22082 using *A. nidulans* NRRL 8112

In order to provide a larger volume of inoculum, 10 ml. of the above-described incubated vegetative medium was used to inoculate 200 ml. of a second-stage vegetative growth medium having the same composition as that of the vegetative medium. This second-stage medium was incubated in a 2-liter wide-mouth Erlenmeyer flask at 25° C. for 48 hours on a shaker rotating through an arc 2 inches in diameter at 250 RPM.

Incubated second-stage vegetative medium (800 ml.) prepared as above-described, was used to inoculate 100 liters of sterile production medium having the following composition:

| Ingredient | Amount (percent) |
| --- | --- |
| Sucrose | 2.0 |
| Maltose | 1.0 |
| Malt extract | 1.0 |
| Molasses | 0.5 |
| Corn steep liquor | 0.5 |
| Enzymatic hydrolysate of casein* | 0.5 |
| Water | 94.5 |

*N-Z-Case, Sheffield Chemical Co., Norwich, N.Y.

The pH of the medium was 7.1 after sterilization by autoclaving at 120° C. for 30 minutes at 15–20 pounds pressure. The inoculated production medium was allowed to ferment in a 165-liter fermentation tank for five days at a temperature of 25° C. The fermentation medium was aerated with sterile air at the rate of 0.4 V/V/M and was stirred with conventional agitators at 250 RPM.

EXAMPLE 2

Separation of the A-22082 Antibiotic Complex

Whole fermentation broth (200 l.), obtained as described in Example 1, was filtered using a filter aid (Hyflo Super-cel, a diatomaceous earth, Johns-Manville Products Corp.). The separated mycelia were extracted with methanol (100 l.). The methanol extract was concentrated under vacuum to a volume of about 50 l. The concentrated methanol extract was acidified to pH 3.5–4.0 by the addition of hydrochloric acid. The resulting solution was extracted twice with ½ volumes of chloroform. The chloroform extracts were combined and concentrated to a volume of about one liter.

A portion of this chloroform concentrate (250 ml.) was added to acetonitrile (100 ml.). The resulting solution was filtered, and the filtrate was concentrated under vacuum to a volume of about 150 ml. This concentrated filtrate was applied to a silica-gel column (5.5 × 54 cm.; Woelm silica gel). The column was eluted with acetonitrile:water (97:3) at a flow rate of 5 ml. per minute, collecting fractions having a volume of approximately 10 ml. Elution was monitored by silica-gel thin-layer chromatography, using a benzene-methanol (7:3) solvent system. The presence of the A-22082 antibiotic complex was detected by bioautography using *Candida albicans*. Column fractions 136–190 contained the A-22082 antibiotic complex. These fractions were combined and evaporated under vacuum to give 453 mg. of the A-22082 antibiotic complex.

EXAMPLE 3

Isolation of Antibiotic A-22082

A portion of the A-22082 antibiotic complex (200 mg.), obtained as described in Example 2, was chromatographed on a silica-gel column (1.5 × 6.0 cm.; Woelm silica gel). The column was eluted with acetonitrile:water (95:5) at a flow rate of one ml. per min., collecting 5-ml. fractions. The fractions were monitored as described in Example 2. Fractions 1-3 which contained antibiotic A-22082 were combined and concentrated under vacuum to an oil. This oil was again chromatographed on a silica-gel column (1.5 × 12 cm.; Woelm silica gel), eluting with acetonitrile:water (97:3). Fractions 15–20 which contained antibiotic A-22082 were combined and concentrated under vacuum to an oil. This oil was dissolved in methanol (2 ml.); the methanol solution was added to diethyl ether (20 ml.). The precipitate which formed was separated by filtration and dried to give 35 mg. of antibiotic A-22082.

EXAMPLE 4

A. Shake-flask Fermentation of A-22082 using *A. rugulosus* NRRL 8113

A culture of *Aspergillus rugulosus* NRRL 8113 was prepared and maintained on an 18- × 150-ml. agar slant having the following composition:

| Ingredient | Amount (percent) |
|---|---|
| Dextrin | 1.0000 |
| Enzymatic hydrolysate of casein* | 0.2000 |
| Yeast extract | 0.1000 |
| Beef extract | 0.1000 |
| KCl | 0.0200 |
| MgSO$_4$ . 7H$_2$O | 0.0200 |
| FeSO$_4$ . 7H$_2$O | 0.0004 |
| Water | 98.5596 |

*N-Z-Amine A, Sheffield Chemical Co., Norwich, N.Y.

The slant was inoculated with *Aspergillus rugulosus* NRRL 8113, and the inoculated slant was incubated at 25° C. for about 7 days. The mature slant culture was covered with beef serum and scraped with a sterile loop to loosen the spores. One-half of the resulting suspension was used to inoculate 50 ml. of a vegetative medium having the following composition:

| Ingredient | Amount (percent) |
|---|---|
| Sucrose | 2.5 |
| Molasses | 3.6 |
| Corn steep liquor | 0.6 |

-continued

| Ingredient | Amount (percent) |
|---|---|
| Enzymatic hydrolysate of casein* | 1.0 |
| K$_2$HPO$_4$ | 0.2 |
| Water | 92.1 |

*N-Z-Case, Sheffield Chemical Co., Norwich, N.Y.

The inoculated vegetative medium was incubated in a 250-ml. wide-mouth Erlenmeyer flask at 25° C. for 24 hours on a shaker rotating through an arc 2 inches in diameter at 250 RPM.

This incubated vegetative medium may be used directly to inoculate the second-stage vegetative medium. Alternatively and preferably, it can be stored for later use by maintaining the culture in the vapor phase of liquid nitrogen. The culture is prepared for such storage in multiple small vials as follows: In each vial is placed 2 ml. of incubated vegetative medium and 2 ml. of a glycerol-lactose solution having the following composition:

| Ingredient | Amount |
|---|---|
| Glycerol | 20% |
| Lactose | 10% |
| Deionized water | 70% |

The prepared suspensions are stored in the vapor phase of liquid nitrogen.

A stored suspension (1 ml.) thus prepared was used to inoculate 50 ml. of a first-stage vegetative medium having the same composition earlier described for the vegetative medium. The inoculated first-stage vegetative medium was incubated in a 250-ml. wide-mouth Erlenmeyer flask at 25° C. for 22 hours on a shaker rotating through an arc 2 inches in diameter at 250 RPM.

B. Tank Fermentation

In order to provide a larger volume of inoculum, 10 ml. of the above-described incubated first-stage vegetative medium was used to inoculate 400 ml. of a second-stage vegetative growth medium having the same composition as that of the vegetative medium. This second-stage medium was incubated in a 2-liter wide-mouth Erlenmeyer flask at 25° C. for 25 hours on a shaker rotating through an arc two inches in diameter at 250 RPM.

Incubated second-stage vegetative medium (800 ml.), prepared as above-described, was used to inoculate 100 liters of sterile production medium having the following composition:

| Ingredient | Amount |
|---|---|
| Glucose | 25 g/liter |
| Starch | 10 g/liter |
| Peptone* | 10 g/liter |
| Blackstrap molasses | 5 g/liter |
| Enzymatic hydrolysate of casein** | 4 g/liter |
| MgSO$_4$ . 7H$_2$O | 0.5 g/liter |
| Czapek's mineral stock*** | 2.0 ml/liter |
| CaCO$_3$ | 2.0 g/liter |
| Deionized water | q.s. 1 liter |
| CaCO$_3$ | 2.0 g/liter |
| Deionized water | q.s. 1 liter |

*W.P. No. 159, Inolex Biomedical Corp., Glenwood, Ill.
**N-Z Amine A, Sheffield Chemical Co., Norwich, N.Y.
***Czapek's mineral stock has the following composition:

-continued

| Ingredient | Amount |
|---|---|
| FeSO$_4$·7H$_2$O (dissolved in 2 ml.[4] conc HCl) | 2 g. |
| KCl | 100 g. |
| MgSO$_4$·7H$_2$O | 100 g. |
| Deionized water | q.s. to 1 litter |

The pH of the medium was 6.8 after sterilization by autoclaving at 121° C. for 30 min. at about 16–18 pounds pressure. The inoculated production medium was allowed to ferment in a 165-liter fermentation tank at a temperature of 25° C. for 4 days. The fermentation medium was aerated with sterile air at the rate of 0.5 V/V/M. The fermentation medium was stirred with conventional agitators at 300 RPM.

EXAMPLE 5

Separation of the A-30912 Antibiotic Complex

Whole fermentation broth (200 l.), obtained by the method described in Example 4, was stirred thoroughly with methanol (200 l.) for one hour and then was filtered, using a filter aid (Hyflo Super-cel, a diatomaceous earth, Johns-Manville Products Corp.). The pH of the filtrate was adjusted to pH 4.0 by the addition of 5 N HCl. The acidified filtrate was extracted twice with equal volumes of chloroform. The chloroform extracts were combined and concentrated under vacuum to a volume of about four liters. This concentrate was added to about 60 liters of diethyl ether to precipitate the A-30912 complex. The precipitate was separated by filtration and dried to give 38 g. of the A-30912 antibiotic complex as a gray powder. The filtrate was concentrated under vacuum to give an oil; this oil was dissolved in methanol (500 ml.). The methanol solution was added to diethyl ether (7.5 l.) to precipitate additional A-30912 complex. This precipitate was also separated by filtration and dried to give an additional 3.5 g. of the A-30912 antibiotic complex.

EXAMPLE 6

Isolation of Antibiotic A-22082 (A-30912 Factor A)

A-30912 antibiotic complex (20 g.), obtained as described in Example 5, was placed on a silica-gel column (4- × 107-cm.; Woelm) in acetonitrile:water (95:5) at a flow rate of 1 to 2 ml. per minute, collecting fractions having a volume of approximately 20 ml. Fractions were checked by thin-layer silica-gel chromatography, using the acetonitrile:water (95:5) solvent system and *Candida albicans* bioautography.

Fractions 74 through 125 were combined and concentrated. The concentrated solution crystallized upon standing to give an additional 124 mg. of sterigmatocystin. Fractions 438 through 481 were combined and concentrated under vacuum to give an oil. This oil was dissolved in a small volume of methanol; and the methanol solution was added to diethyl ether (15 volumes). The precipitate which formed was separated and dried to give 2.17 g. of antibiotic A-22082 (A-30912 factor A).

We claim:

1. Antibiotic A-22082 which is a white amorphous solid; which is soluble in methanol, ethanol, dimethylformamide, dimethyl sulfoxide, ethyl acetate or in aqueous solutions having a pH greater than 7.0; but which is insoluble in diethyl ether or petroleum ether; and which has:

a. an approximate molecular weight of 1100, as determined by mass spectrometry and titration;
b. an approximate elemental composition of 56.52 percent carbon; 7.29 percent hydrogen, 8.68 percent nitrogen, and 27.09 percent oxygen;
c. an approximate empirical formula of $C_{51-53}H_{79-83}N_7O_{17-19}$;
d. the following specific rotations:
   $[\alpha]_D^{25}$ −44° (c0.5, CH$_3$OH)
   $[\alpha]_{365}^{25}$ −156° (c0.5, CH$_3$OH)
e. an infrared absorption spectrum in KBr disc with the following observable characteristic absorption maxima: 2.97 (strong), 3.30 (weak); 3.36 (shoulder), 3.39 (medium), 3.47 (weak), 5.97 (strong), 6.06 (strong), 6.45 (medium), 6.53 (medium), 6.83 (medium), 7.78 (weak), 8.00 (weak), 9.07 (weak) and 11.66 (weak) microns;
f. ultraviolet absorption spectra in both neutral and acidic methanol with absorption maxima at 225 nm ($\epsilon$ 18,000), 275 nm ($\epsilon$ 3,000) and 284 nm (shoulder $\epsilon$ 2,500) and absorption maxima in basic methanol at 245 nm ($\epsilon$ 16,000) and 290 nm ($\epsilon$ 3,000);
g. a $^{13}$C nuclear magnetic resonance spectrum in perdeuteromethanol with the following characteristics:
   δ 176.1, 174.3, 173.4, 172.7, 172.4, 169.8, 158.4, 132.8, 130.9, 129.6, 129.0, 116.2, 77.0, 75.7, 74.4, 71.3, 70.9, 69.6, 68.3, 62.4, 58.7, 56.9, 56.1, 52.9, 39.0, 38.5, 36.8, 35.2, 33.9, 32.9, 32.6, 30.7, 30.4, 30.2, 28.2, 27.0, 26.5, 23.6, 20.1, 19.6, 14.4, and 11.3 ppm;
h. a titratable group with a p$K_a$ value of 12.7 in 66% aqueous dimethylformamide;
i. after hydrolysis, an amino-acid analysis which indicates the presence of threonine, hydroxyproline, and three other as-yet-unidentified amino acids;
j. an $R_f$ value of 0.35 on silica-gel thin-layer chromatography using a benzene:methanol (7:3) solvent system and *Candida albicans* bioautography for detection;
k. the following $R_f$ values in the paper chromatographic systems indicated below, using *Candida albicans* bioautography for detection:

| $R_f$ Value | Solvent System |
|---|---|
| 0.76 | Butanol saturated with water |
| 0.69 | Butanol saturated with water plus 2% p-toluenesulfonic acid |
| 0.75 | Methanol:0.1 N HCl (3:1) |
| 0.17 | Butanol:ethanol:water (13.5:15:150) |
| 0.78 | Methanol:0.05 M sodium citrate at pH 5.7 (7:3); paper buffered with 0.05 M sodium citrate at pH 5.7 |

2. The method of producing antibiotic A-22082 as defined in claim 1 which comprises cultivating *Aspergillus nidulans* NRRL 8112 in a culture medium containing assimilable sources of carbohydrate, nitrogen, and inorganic salts under submerged aerobic fermentation conditions until a substantial amount of antibiotic activity is produced by said organism in said culture medium.

3. The method of claim 2 which includes the additional step of separating antibiotic A-22082.

* * * * *

Notice of Adverse Decision in Interference

In Interference No. 100,072, involving Patent No. 4,024,246, C. E. Higgens and K. H. Michel, ANTIBIOTIC A-22082 AND PROCESS FOR PRODUCTION THEREOF, final judgment adverse to the patentees was rendered Sept. 10, 1981, as to claim 1.

[*Official Gazette March 7, 1989.*]